United States Patent
Ribault et al.

(10) Patent No.: US 6,488,639 B1
(45) Date of Patent: Dec. 3, 2002

(54) FREQUENCY ADJUSTMENT IN HIGH INTENSITY FOCUSED ULTRASOUND TREATMENT APPARATUS

(75) Inventors: Mathieu Ribault, Lyons (FR); Francois LaCoste, Rueil Malmaison (FR); Jean-Yves Chapelon, Villeurbanne (FR); Emmanuel Blanc, St. Genis Laval (FR)

(73) Assignees: Technomed Medical Systems, S.A, Vaulx-en-Velin (FR); Institut National de La Santa et de La Recherche Medicale, Paris (FR)

( * ) Notice: Subject to any disclaimer, the term of this patent is extended or adjusted under 35 U.S.C. 154(b) by 0 days.

(21) Appl. No.: 09/700,145
(22) PCT Filed: May 12, 1999
(86) PCT No.: PCT/FR99/01151
§ 371 (c)(1),
(2), (4) Date: Jan. 5, 2001
(87) PCT Pub. No.: WO99/58196
PCT Pub. Date: Nov. 18, 1999

(30) Foreign Application Priority Data

May 13, 1998 (FR) .......................................... 98 06043

(51) Int. Cl.⁷ ............................................. A61B 17/22
(52) U.S. Cl. ................................... 601/2; 600/439
(58) Field of Search .................... 601/2–4; 600/439, 600/459; 310/320, 334

(56) References Cited

U.S. PATENT DOCUMENTS

| | | | | |
|---|---|---|---|---|
| 4,960,109 A | * | 10/1990 | Lele | 600/549 |
| 5,391,140 A | * | 2/1995 | Schaetzle et al. | 601/4 |
| 5,665,054 A | * | 9/1997 | Dory | 601/3 |
| 5,795,311 A | * | 8/1998 | Wess | 601/2 |
| 5,984,881 A | * | 11/1999 | Ishibashi et al. | 601/2 |
| 6,007,499 A | * | 12/1999 | Martin et al. | 601/3 |
| 6,042,556 A | * | 3/2000 | Beach et al. | 601/3 |
| 6,309,355 B1 | * | 10/2001 | Cain et al. | 600/439 |

FOREIGN PATENT DOCUMENTS

| | | | | |
|---|---|---|---|---|
| EP | 0 248 532 A1 | * | 12/1987 | A61H/23/00 |
| EP | 0 351 610 A2 | * | 1/1990 | A61B/19/00 |
| EP | 0 685 211 A1 | * | 12/1995 | A61F/7/00 |
| EP | 0 734 742 A2 | * | 10/1996 | A61N/7/00 |

OTHER PUBLICATIONS

J.P. Do–Huu, P. Hartemann, *Annular Array Transducer for Deep Acoustic Hyperthermia*, IEEE Ultrasonics Symposium, vol. 81CH1689–9, pp. 705–710, 1981.

C.A. Caln, S.I. Umemura, *Concentric–Ring and Sector–Vortex Phased–Array Applicators for Ultrasound Hyperthemia Therapy*, IEEE Transactions on Microwave Theory and Techniques, vol. MTT–34, pp. 542–551, 1986.

E.S. Ebbini, C.A. Cain, *A Spherical–Section Ultrasound Phased Array Applicator for Deep Localized Hyperthermia*, IEEE Trans Biomed Eng., vol. 38, pp. 634–643, 1991.

J.V. Chapelon et al., *The Feasibility of Tissue Ablation Using High Intensity Electronically Focused Ultrasound*, IEEE Ultrasonics Symp., vol. 93CH3301–9, pp. 1211–1214, 1993 proposed using annular phased arrays for HIFU.

(List continued on next page.)

Primary Examiner—Marvin M. Lateef
Assistant Examiner—Shawna J Shaw
(74) Attorney, Agent, or Firm—Welsh & Katz, Ltd.

(57) ABSTRACT

The invention concerns an apparatus for treating a biological sample by emitting focused high intensity ultrasounds towards a focal point, characterised in that it comprises means emitting wideband focused ultrasounds. The apparatus enables to adjust the focused ultrasound frequency according to the target attenuation, the thickness of the tissues traversed, the temperature evolution, or the lesion displacement during emission.

17 Claims, 1 Drawing Sheet

OTHER PUBLICATIONS

K. Hynynen et al., *Feasibility of Using Ultrasound Phased Rays for MRI Monitored Noninvasive Surgery*, IEEE Trans UFFC, vol. 43, No. 6, 1996 proposes HIFU treatments.

C.R. Hill, *Optlmum Acoustic Frequency for Focused Ultrasound Surgery*, in Ultrasound in Med & Biol; vol. 20, No. 3, pp. 271–277; 1994.

*Lesion Development in Focused Ultrasound Surgery: a General Model* in Ultrasound in Med & Biol; vol. 20, No. 3, pp.259–269, 1994.

J. Ophir et al., *Attenuation Estimation in Reflection: Progress and Prospects*, Ultrasound Imaging 6, pp. 349–395, 1984.

H.F. Bowman, *The Bio–heat Transfer Equation and Discrimination of Thermally Significant Vessels*, Annals New York Academy of Sciences. No. 335, pp. 155–160, 1981.

S.A. Saparto, W.C. Dewey, *Thermal Dose Determination in Cancer Therapy*, Int. J. Radiation Oncology Biol. Phys. No. 10, pp. 787–800, 1984.

\* cited by examiner

FREQUENCY ADJUSTMENT IN HIGH INTENSITY FOCUSED ULTRASOUND TREATMENT APPARATUS

BACKGROUND OF THE INVENTION

This invention relates to apparatus for treating a biological target by delivering focused ultrasound at high intensity to a focal point. It further relates to a method for adjusting the frequency of apparatus for treating a biological target by delivering high intensity focused ultrasound to a focal point.

The invention falls in the field of tissue treatment using focused ultrasound, and more particularly the field of tissue destruction inside an organism by creation of high temperatures using focused ultrasound.

In the general field of focused ultrasound, as the person skilled in the art knows, various types of treatment can be distinguished: the treatment that has been around longest is treatment by lithotripsy, which applies to destroying hard bodies; this type of treatment uses shock waves, i.e. short high power pulses. Later, it was proposed to treat soft issue by hyperthermia, by heating tissue to slightly elevated temperatures, i.e. less than 45° C. Hyperthermia involves emitting ultrasound in the form of long and lower power pulses to the tissue to be treated. Finally, currently, treatment of soft tissue using high intensity focused ultrasound, generally called HIFU (high intensity focused ultrasound) is being proposed. HIFU treatment involves heating tissue to elevated temperatures, typically greater than 45° C.

These various types of treatment involve very different technical problems, both as regards sending and focusing of the ultrasound as well as its propagation.

HIFU treatment raises different problems. Generally speaking, the aim is to improve effectiveness of treatment, i.e. destruction of selected tissue. For this, the first problem resides in a suitable choice of the ultrasound transmission parameters; the latter, and in particular ultrasound frequency, need to be chosen very accurately. They generally depend on numerous factors such as: target depth, nature of tissue, type of necrosis desired.

A second problem is that of gaining access to the targets or tissue to be treated. Due to patient anatomy, targets are sometimes difficult to get at for ultrasound beams. Moving the transducer has been proposed; moving the transducer may however also be limited by patient morphology. In prostate treatment by endorectal probe, various solutions to this problem have been proposed, see for example French Patent applications serial numbers 9102620, 9309158, 9608096, 9401304, 9406539. These various solutions could still be improved, for ensuring better treatment, in precise areas, by hyperthermia or HIFU.

A third problem resides in the fact that the beam emitted by an ultrasound focused transducer is generally effective within a fixed region, called the focal zone. Now, this focal zone most frequently is smaller than the size of the target tissue. Treatment of extensive targets is consequently a problem. One proposition was to successively employ, by endorectal route, transducers of various focal lengths, for example, in the case of the prostate, a first one, of short focal length, suitable for treating the posterior region and another one, of longer focal length, for the anterior region. This method involves changing the probe during the session, which is not desirable.

One proposed solution to this third problem consisted in employing variable focal length transducers. These can be constructed from an array of individual transducers. Do-Huu was the first to employ annular arrays for hyperthermia ((JP Do-Huu, P Hartmann, *Annular array transducer for deep acoustic hyperthermia*, IEEE Ultrasonics Symp, Vol 81CH1689-9, pp. 705–710, 1981, or U.S. Pat. No. 4,586,512 of May, 1986). Still for hyperthermia, we can cite the work of Cain (C A Cain, S A Umemura, *Concentric-ring and sector vortex phased array applicators for ultrasound hyperthermia therapy*, IEEE Trans Microwave Theory Tech, vol MTT-34, pp 542–551, 1986) and the work of Ebbini (E S Ebbini, C A Cain, *A spherical-section ultrasound phased array applicator for deep localized hyperthermia*, IEEE Trans Biomed Eng, vol 38, pp 634–643, 1991).

J Y Chapelon et al, *The feasibility of tissue ablation using high intensity electronically focused ultrasound*, IEEE Ultrasonics Symp, Vol 93CH3301-9, pp 1211–1214, 1993 proposed using annular phased arrays for HIFU.

The work of Hynynen and corresponding publications, for example K Hynynen et al, *Feasibility of using ultrasound phased rays for MRI monitored noninvasive surgery*, IEEE Trans UFFC, Vol 43, No. 6, 1996 proposes HIFU treatments.

A variable focal length transducer can also be constructed using a fixed focus transducer and an acoustic lens, as disclosed in French patent 2,715,822 in the name of Dory.

In every case, it is essential to adapt treatment parameters to target depth for obtaining satisfactory therapeutic effect. In particular, the operating frequency of the transducer must be determined. This is calculated from the equation giving absorbed acoustic power per unit of volume (W/cm$^3$) at the focus of a focused transducer:

$$Q = 2\alpha F I_0 G e^{-2\alpha F d} \tag{1}$$

where:

Q is the acoustic power absorbed per unit of volume $\alpha$ is the acoustic attenuation factor (Neper/cm/MHz)

$I_0$ is the acoustic intensity at the transducer emission surface (W/cm$^2$)

G is antenna gain

F is frequency (MHz)

d is the thickness of the absorbing medium (cm) as explained in Hill C. R. *Optimum acoustic frequency for focused ultrasound surgery* in Ultrasound in Med & Biol; 20; 271–277; 1994 and *Lesion development in focused ultrasound surgery: a general model* in Ultrasound in Med & Biol; 20; 259–269; 1994.

This formal approach is known and employed by designers of apparatus for tissue treatment by focused ultrasound, for determining optimum operating frequency of a therapy transducer depending on depth or acoustic attenuation of the intended target. This choice is defined a priori and remains fixed for a given transducer.

Seppi, in U.S. Pat. No. 4,875,487 discloses, for hyperthermia, use of wideband transducers and choice of working frequency range depending on target depth. That Patent additionally proposes employing a wideband signal so as to create incoherent beams which are, consequently, unfocused.

European patent application 0,351,610 discloses wideband transducers focused electronically, focusing being controlled as a function of cavitation.

SUMMARY OF THE INVENTION

This invention proposes an elegant and simple solution to the problem of distributing acoustic power in ultrasound treatment; it ensures better control of overall power, and good definition of the region treated.

More precisely, the invention provides apparatus for treating a biological target by emitting high power focused ultrasound towards a focal point, comprising wideband transducer means for emitting ultrasound, means for controlling said transducer means for emitting focused ultrasound over a narrow frequency range, and means for adjusting the frequency range of said controlling means as a function of measurement results.

According to one embodiment of the apparatus, the means for emitting ultrasound have a variable focal length.

According to a further embodiment, the apparatus additionally comprises coupling means of variable thickness adjacent to said ultrasound emitting means.

The ultrasound emitting means preferably have a fixed focal length and the apparatus can additionally comprise variable thickness coupling means adjacent to the emitting means.

According to one embodiment, the apparatus additionally comprises means for measuring acoustic attenuation in the region of a focal point, the means for adjusting frequency range performing adjustment of the focused ultrasound frequency range as a function of results supplied by acoustic attenuation measurement means.

The apparatus preferably comprises means for measuring mean acoustic attenuation variation close to a focal point, and the means for adjusting frequency range performing adjustment of a focused ultrasound frequency range as a function of results supplied by the means for measuring mean acoustic attenuation variation.

According to one embodiment, the apparatus additionally comprises means for calculating or measuring temperature in the region of a focal point, and the means for adjusting frequency range perform adjustment of the focused ultrasound frequency range as a function of results supplied by said means for calculating or measuring temperature.

According to a further embodiment, the apparatus comprises means for determining the thickness of. tissue through which ultrasound has passed, and the means for adjusting frequency range perform adjustment of the focused ultrasound frequency range as a function of results supplied by said thickness-determining means.

The means for determining a thickness of tissue through which ultrasound has passed preferably comprises means for measuring thickness of variable-thickness coupling means.

According to one embodiment, the apparatus comprises means for calculating a displacement of a lesion as a function of time of shooting, and for calculating thickness through which ultrasound has passed, the adjustment means performing focused ultrasound frequency adjustment as a function of of displacement and thickness.

According to a further embodiment, the apparatus comprises means for calculating lesion depth as a function of shooting time, the adjustment means performing adjustment of focused ultrasound frequency as a function of depth.

In one embodiment, the adjustment means perform adjustment of frequency range before a shot.

In a further embodiment, the adjustment means perform frequency range adjustment during a shot.

A method for adjusting the frequency of apparatus for treating a biological target by emitting high intensity focused ultrasound towards a focal point is provided, the method comprising the steps of:

measuring attenuation or variation in attenuation of a biological target; and adjusting focused ultrasound frequency as a function of measured attenuation.

A method for adjusting the frequency of apparatus for treating a biological target by emitting high intensity focused ultrasound towards a focal point is also provided comprising the steps of:

measuring a thickness of tissue through which ultrasound has passed; and adjusting focused ultrasound frequency as a function of this thickness.

Measurement of tissue thickness through which ultrasound has passed can comprise the steps of:

calculating a focal length between an ultrasound sender and a focal point;

measuring the distance between the sender and a first interface with a body containing the target; and subtracting a distance between the sender and the first interface from focal length in order to obtain a thickness of tissue through which ultrasound has passed.

Ultrasound frequency adjustment is preferably performed so as to apply a given power Q to a target.

Ultrasound frequency adjustment is advantageously performed by application of the following formula:

$$Q = 2\alpha F I_0 G e^{-2\alpha F d} \qquad (1)$$

where:

Q is the acoustic power absorbed per unit of volume $\alpha$ is the acoustic attenuation factor (Neper/cm/MHz)

$I_0$ is the acoustic intensity at the transducer emission surface (W/cm$^2$)

G is antenna gain

F is frequency (MHz)

d is the thickness of the absorbing medium (cm).

In one embodiment of the method, the step of frequency adjustment is performed before a shot.

In another embodiment, the step of frequency adjustment is performed during a shot.

Further characteristics and advantages of the invention will become clear from the description which follows of some embodiments, provided by way of example and with reference to the attached drawings.

DETAILED DESCRIPTION OF THE PREFERRED EMBODIMENTS

Figure 1:
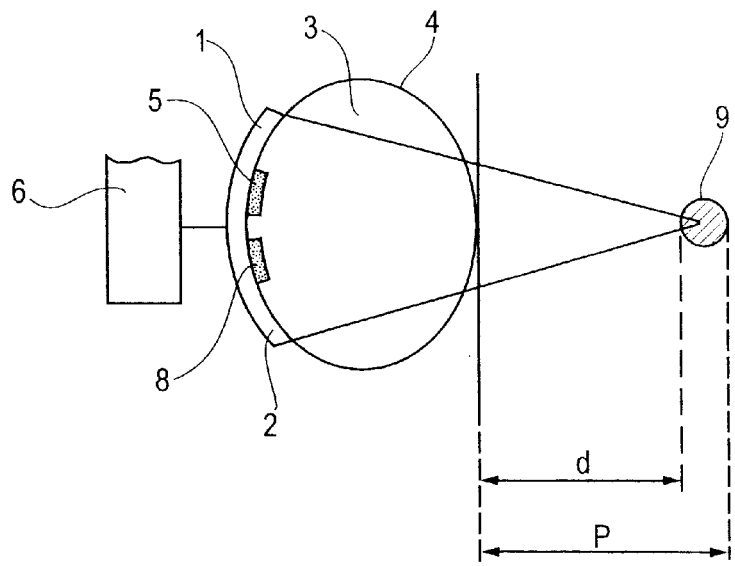
FIG. 1 is a diagrammatical view of HIFU apparatus for carrying out the invention.

The invention proposes, in HIFU apparatus, to make the ultrasound frequency used vary as a function of the measured acoustic attenuation of the target, or of variations in the measured attenuation. It also proposes employing wideband ultrasound emitting means, for emitting ultrasound in a narrow frequency band, this frequency band varying as a function of the measured attenuation or attenuation variation.

The invention goes against the teaching of prior art documents which disclose the use of wideband transducers. In these documents, wideband transducers are employed for emitting ultrasound over a wide frequency range and hot for emitting ultrasound over a narrow frequency band.

For the person skilled in the art, or the specialist in focused ultrasound, the term "wideband" covers around 50% of the central frequency, equivalent for example to 2–3 MHz. The frequencies habitually employed in therapy by hyperthermia or HIFU are in general comprised between 1 MHz and 5 MHz.

Inversely, the term "narrowband" signifies, for the person skilled in the art, a reduced frequency range with respect to the central frequency; "single frequency" means a range of frequencies as reduced as possible, taking account of technical constraints on the emitting equipment; ultrasound emission for therapeutic purposes is generally considered as single frequency when the range of frequencies transmitted is less than about 5% of the ultrasound central frequency.

The invention also proposes a solution to the new problem of variation in attenuation as a function of the target and of individual patients. It is based upon the surprising finding that acoustic attenuation varies from one patient to another, even for the same tissue. On a sample as limited as 30 persons, measurements performed on the prostate show that acoustic attenuation varies from one patient to the next in a ratio of around 50%. This introduces a fresh problem of the deterioration in reproduceability of treatment, and which is incompatible with good treatment effectiveness.

The invention also goes against a fairly widespread prejudice in the prior art: in all the documents discussing HIFU, the calculations make reference to a fixed value for tissue attenuation. This value generally is taken from publications. It is consequently generally accepted that a given tissue will have a fixed acoustic attenuation value.

Contrary to this prejudice, the invention proposes adapting transducer operating frequency not only to the type of target organ but also to the specific patient concerned. Advantageously, this measurement can be made prior to each treatment, thereby allowing the optimum frequency of the HIFU apparatus to be adjusted, for example using formula (1) above.

Various solutions are possible for measuring acoustic attenuation. Measurement is advantageously performed by attenuation measurement in the reflection mode. Ophir made an inventory of biological tissue attenuation measurement techniques using reflection (J. Ophir, T. H. Shawker, N. F. Maklad, J. G. Miller, Stephen W. Flax, P. A. Narayana and J. P. Jones, "Attenuation estimation in reflection: progress and prospects", Ultrasonic Imaging 6, pp 349–395, 1984). Generally speaking, two types of method for measuring attenuation in biological tissue can be distinguished: frequency methods and time methods. The time methods are better adapted to real time whereas the frequency methods provide finer measurement and are flexible, but require a larger computing overhead.

Frequency methods are principally of two types: spectral differential methods where the information is contained in the variation of amplitude of various spectral components, and spectral shift methods where the information is contained in signal central frequency shift.

Time (temporal) methods can also be divided into two categories. Firstly, they comprise methods employing the echographic signal amplitude which are the wideband or narrow band amplitude attenuation estimation methods. Secondly, they comprise time methods giving information on how the central frequency of a signal is changing (zero crossing density methods). These various methods can be employed for carrying out the invention.

Once the measurement has been performed, using, for example, one or the other of these methods, the optimum frequency for HIFU treatment is deduced from the measurement results. A determination of this frequency can advantageously be performed by applying equation (1) above. Applying this formula makes it possible to calculate optimum frequency for a given amount of energy to be applied to the target; for this, all that is needed is to reverse formula (1) to obtain the frequency value as a function of attenuation.

The invention can readily be carried out in the apparatus described below with reference to FIG. 1 et seq.

In another embodiment, in HIFU apparatus, the frequency of the ultrasound employed is varied as a function of target tissue temperature. The invention now provides a solution to the new problem of variation in attenuation as a function of target temperature. In effect, the attenuation factor varies with temperature in particular when this exceeds 50° C. As variation for tissue subjected to thermal treatment can be twice its value at 37° C., the invention allows better use of the energy, and application of treatment to a more precise region.

Contrary to all apparatus of the prior art, in which this variation is not taken into consideration or simply ignored, the invention proposes varying frequency during the duration of a shot. As was the case above, the variation in frequency during a shot can be obtained by applying formula (1). For this, for a determined target acoustic power, formula (1) is reversed and the optimum frequency as a function of the target temperature is found. Target temperature can be measured by MRI during treatment; it could also be calculated using the so-called bioheat equation which describes changes of heat during a shot. This equation is given in the publications covering tissue hyperthermia such as for example in Bowman HF "The bioheat transfer equation and discrimination of thermally significant vessels" ann. New York Acad. of Sci. No. 335 pp 155–160, 1981. The bioheat equation also makes it possible to calculate the thermal dose needed for tissue necrosis as explained, for example, in Sapareto S A and Dewey W C "Thermal dose determination in cancer therapy" Int. J. Radiation Oncology Biol. Phys. N°10 pp 787–800, 1984.

The invention makes it possible to optimize heat delivery around the focus, increase the speed with which elementary lesions are formed thereby decreasing the duration of treatment.

This variation in frequency during treatment can be employed independently of, or in combination with, frequency variation prior to treatment. The invention that has just been described can be implemented in an apparatus of the type described below with reference to FIG. 1 et seq.

The invention further proposes, in HIFU apparatus, to vary frequency as a function of the thickness of the tissue through which the energy passes. In practice, ultrasound treatment transducers are not in direct contact with the target or tissue and the ultrasound firstly passes through a coupling fluid. The latter is generally contained in a pocket that is applied to the tissue. To reach targets at a greater or lesser depth, the position of the transducer is adjusted along the acoustic axes. This means that the distance covered by the ultrasound in patient tissue can vary.

It is proposed, in order to optimise effectiveness, to adapt or vary ultrasound emitting frequency as a function of the thickness of tissue actually passed through. This thickness can for example be calculated by subtraction, knowing the focal length and measurement distance between the transducer and the first tissue interface. The latter can for instance be determined by the technique described in French patent application serial No. 9406539.

Formula (1) can now be applied for determining optimum frequency, for a given power Q, as a function of the thickness of absorbent medium d. For this, it is sufficient to reverse formula (1) to obtain F as a function of d. Assuming this, we can ignore losses in the coupling medium, which is legitimate for water, generally employed as the coupling medium.

The invention ensures that a given transducer is effective both for deep shots as well as for surface shots. It avoids shots that are too powerful and low depth burns.

Variation in frequency according to the invention can be performed before or during treatment. It can be combined with variation in frequency as a function of target attenuation, calculated before shooting. It can also be combined with frequency variation as a function of target temperature. It can also be used alone. The invention just described can be implemented in an apparatus of the type described below with reference to FIG. 1 et seq.

The invention further proposes a solution to the new problem of lesion progression during firing. This is based on a new finding that, in HIFU apparatus, the biological lesion in tissue originates close to the focal point and progresses towards the transducer at depths which consequently become smaller and smaller. This is the origin of a new problem in that the frequencies chosen for one given depth of shooting are not necessarily the most suitable during shooting if the biological lesion is formed at variable depths. Thus, if frequency was chosen optimally for lesion creation at the focal point, it becomes less and less suitable as the lesion approaches the transducers. In practice, this is reflected by a loss of efficiency during shooting. For example, a few milliseconds are enough to form a 5–10 mm lesion at the focal point but several seconds are needed for it to develop over some 20 mm in front of the focal point. With firing durations exceeding several seconds, the effects of spread of heat are not negligible and can give rise to lesions the extent of which is hard to control. In this case, it is appropriate to adapt operating frequency to the displacement of the lesion.

The invention consequently proposes adapting the frequency over time, as a function of lesion displacement and consequently of the depth thereof. The law governing collision displacement can be determined not only experimentally but also by simulation from a mathematical model. Frequency can then be adapted using formula (1), taking account of variation, brought about by shifting of the lesion, in the thickness of tissue passed through. One can also simply use the typical frequency values given in the various embodiments described below.

In one embodiment, the invention is adapted to the case of a fixed focal length transducer for which lesion formation is accompanied by change of frequency during the shot. The table below gives examples of values for lesion dimension depending on shot duration. These values were obtained from experiments on animals.

| Duration of shot/dimension of lesion | depth of lesion P (mm) | base distance from lesion to surface d (mm) | length of lesion (P − d) in mm |
|---|---|---|---|
| 2 sec | 17 | 7 | 10 |
| 4.5 sec | 18 | 0 | 18 |

The depth P of the lesion is the distance between the point on the lesion furthest from the surface—typically the surface of the patient's skin, or, in the case of endocavital treatment, the inner surface of the cavity used for treatment—and this surface. The distance d is the distance between the point on the lesion closest to the surface, and the surface. These two distances are shown on FIG. 1.

After 2 seconds shooting, the base of the lesion was situated at a depth of 7 mm and was 10 mm long. Between 2 and 4.5 seconds shooting, the lesion extended to reach the surface. We note thus that lesion depth varies during shooting and that the lesion progresses towards the surface; the invention proposes making use of this surprising finding to make an appropriate adjustment to frequency. One can for example employ a low frequency at the beginning of firing to initiate a deep lesion and then high frequencies at the end of shooting when the lesion is close to the surface. The following firing sequence is for example proposed:

| Time (s) | 0–1 | 1–2 | 2–3 | 3–4 |
|---|---|---|---|---|
| Frequency (MHz) | 1.8 | 2.25 | 2.75 | 3 |

Stated in other terms, frequency is changed every second, with frequency increasing. This embodiment, in which the frequency is increased by steps, is the most simple to implement; other ways of varying frequency for increasing frequency during firing can be envisaged.

Frequency values given in the table are optimum for an intensity of 1000 to 2000 W/cm$^2$ at the focal point, a 40 mm diameter transducer of focal length 40 mm, such as the applicant's "Ablatherm" apparatus used for endorectal prostate cancer treatment. Frequency values can vary as a function of the treatment being followed and as a function of the transducer and the lesions. The invention consequently provides higher efficiency and better lesion control by ensuring that firing "tracks" lesion formation. The invention, in this embodiment, proposes adapting frequency to the extent of the lesion during treatment.

Just like the case above, the invention can be used in combination with frequency variation as a function of attenuation in the tissue, of tissue temperature, or as a function of the thickness of the coupling means.

The invention also proposes varying the position of the lesion with respect to the fixed focal length type transducer focal point by changing frequency during firing, or between shots. In this embodiment, the invention resides on the finding that tissue attenuation increases with frequency. The energy reaching the focal point consequently decreases as frequency increases and lesion formation occurs ahead of the focal point when frequency increases. The invention proposes proceeding with successive shots at different frequencies.

The following table gives values for lesion position as a function of firing frequency. These values are from experiments carried out on animals.

| Firing frequency/ dimensions of lesions | lesion depth P (mm) | distance between base of lesion and surface d (mm) | length of lesion (p − d) in mm |
|---|---|---|---|
| 1.8 MHz | 23 | 2.7 | 20.3 |
| 2.25 MHz | 21.8 | 1.3 | 20.4 |
| 2.75 MHz | 18.5 | 0 | 18.5 |
| 3 MHz | 20.4 | 0 | 20.4 |

The other treatment parameters are:
Duration of emission for each shot=4.5 s
Idle time following each shot=5 s;
In all cases, the transducer surface was cooled.

For the highest frequencies, lesions are effectively created at lower depth. Lesion length remains fairly constant so that they get formed close to the tissue surface.

To come back to the example of applicant's "Ablatherm" apparatus transducer, the transducer can either be excited at the frequency of 2.25 MHz when it is the heart of the prostate which is being aimed at or, advantageously, at 3 MHz when it is desired to reach the posterior region of the prostate, in particular the capsule of the gland. The invention makes it possible to consequently adapt, for a given focal length and consequently without moving the probe, the depth at which tissue is treated, by simply varying frequency. Using electrical or electronic means, the region treated can be shifted without having recourse to mechanical movement or electronic focusing.

As above, the invention can be used in combination with variation in frequency as a function of attenuation in tissue, tissue temperature or as a function of the thickness of the coupling means.

In all the embodiments described above, the change in frequency can be discrete or continuous. FIG. 1 is a diagrammatical view of HIFU apparatus for carrying out the invention. Apparatus 1 comprises means for emitting high intensity focused ultrasound, for example a cup 2 of composite transducers, or a transducer array. The emitting means are wideband emitting means which focus the ultrasound onto a focal point, and are adapted to emit ultrasound over a range of frequencies having a width of 40% of the central frequency, preferably a width of 50% of the central frequency; values of 2 to 3 MHz for bandwidth are suitable. A band of frequencies of such a width, covering the frequency values given above, is suitable. Such a band of frequencies can be obtained for piezo-composite-type transducers, i.e. transducers composed of a flexible matrix and ceramic transducers, coupling of which is essentially obtained by compressing the flexible matrix; in other words, energy coupling takes place principally not directly from the ceramics but rather via the matrix.

In these embodiments, frequency variations have an effect on the focusing: a higher frequency produces a finer focal spot through diffraction phenomena and, consequently, higher intensity at the focal point for a given emitting power.

The emitting means 1 send ultrasound towards coupling medium 3, for example degassed water, contained in an ultrasound-transparent casing 4.

The apparatus of FIG. 1 further comprises means 5 for measuring acoustic attenuation around the focal point 9 of the emitting means; these means 5 supply the results of measurements to the means 6 for adjusting the focused ultrasound frequency. For acoustic attenuation variation measurement, the solution described in applicant's co-pending French patent application entitled "Method for measuring the effect of treatment on tissue" can notably be employed. This particularly advantageous solution can be used instead of attenuation measurement by a conventional method. As this solution involves measurement before and after shooting, it is advantageously implemented right from the second shot; it has the advantage of being able to be implemented in real time during treatment.

The adjustment means perform focused ultrasound frequency adjustment, for example using equation (1), if needs be with the frequency correction mentioned above. Adjustment can advantageously be done before each shot.

The apparatus of FIG. 1 additionally comprises means 8 for measuring the thickness of tissue passed through, for example for measuring the distance between a fixed point and the casing 4 in contact with the tissue. Knowing the focal length, the means 8 can determine the thickness of tissue passed through. The measurement means can for example employ mode-A echography, as described in French patent application serial number 94.06539. In that application, the transducer is a transducer array the central pad of which is employed for generating acoustic signals allowing attenuation to be measured by A-mode echography.

The results of calculation or measurement are supplied to the adjusting means 6 for focused ultrasound frequency. The means 6 perform frequency adjustment as a function of tissue thickness passed through.

Advantageously, the means 6 are adjustable in different modes, as a function of the type of treatment desired. In a first mode, the adjustment means adjust frequency as a function of attenuation at the target. In a second mode, the adjustment means adjust frequency as a function of the thickness of tissue passed through. In a third adjustment mode, the adjustment means adjust frequency as a function of attenuation at the target and thickness of tissue passed through. In a fourth adjustment mode, the adjustment means adjust frequency as a function of the distance between the base of the lesion and the surface. These adjustment modes make it possible to adjust frequency before each shot, or before a series of shots.

Each of these adjustment modes can be associated with an adjustment mode for frequency during firing; in a fourth adjustment mode, the adjustment means adjust frequency during firing as a function of the lesion temperature; in a fifth adjustment mode, the adjustment means adjust frequency during firing as a function of tissue thickness passed through during firing, taking account of displacement of the lesion during firing. In a sixth adjustment mode, the adjustment means adjust frequency during firing as a function of lesion temperature and the thickness of tissue passed through during a shot, taking account of displacement of the lesion during the shot. These latter three adjustment modes can be combined with the first three modes.

Figure 2:
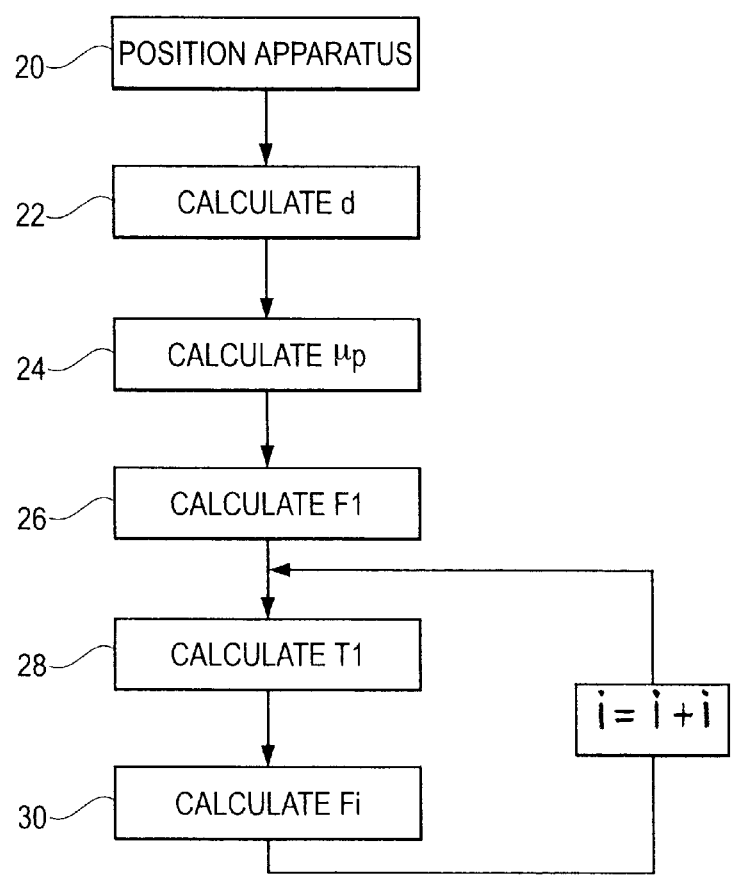
FIG. 2 is a flow chart of one possible procedure for frequency adjustment according to the invention.

FIG. 2 is a flow chart of one possible method for adjusting frequency according to the invention. FIG. 2 shows the example of prostate treatment, using HIFU apparatus with a variable-thickness coupling medium.

At step 20, the apparatus is put into place, and the casing of the coupling medium is put in contact with the patient's body. The focal point of the emitting device is brought close to the target to be treated, by a method known per se, for example by imaging the region surrounding the target, and viewing the focal point on the imaging device screen.

At step 22, the thickness d of the tissue passed through is measured using measuring means 8, knowing the focal length of the transducer.

At step 24, the acoustic attenuation $\mu p$ of the patient's prostate is measured using the means 5 for measuring attenuation.

Knowing d and $\mu p$, the optimum firing frequency F1 is calculated at step 26 for supplying a given energy to the target.

At step 28, knowing the law governing temperature change and the law for displacement of the lesion, the duration t1 of firing is calculated before changing frequency. This calculation, as explained above, is done using the "bioheat" equation; one can also use the experimental values mentioned above.

At step 30, one can then calculate, for the position of the lesion after a period of time t1, and for the temperature after the period of time t1, a new optimum frequency F2, using the new thickness of the tissue passed through and the new attenuation which is a function of the temperature reached.

Steps 28 and 30 are recommended until reaching a duration corresponding to a treatment of the whole of the target.

One can then proceed with the treatment.

Treatment can also be carried out at the same time as calculation of frequency Fi and the time ti for the next firing sequence. This embodiment is advantageous if the new attenuation is being measured continuously or between each shot.

In the description above we have used the word "shot" for delivery of ultrasound at a given frequency; treatment can advantageously comprise a variety of such shots, separated or not separated by intervals during which focused ultrasound is not emitted.

The adjustment of frequency according to the invention is carried out, preferably automatically, as a function of the selected treatment power. The method applies to all treatment powers, and does not provide any suggestion regarding treatment power or total energy to be applied for a given target. In this sense, frequency adjustment according to the invention is only a technical method aimed at resolving the technical problem of optimum distribution of energy in the target, and solely within the target. Adjustment according to the invention is consequently independent of the surgeon practising his art, though the choice of organs to be treated, powers to be applied, duration of treatment or other parameters. Indeed, this adjustment of frequency has no function or relation with the therapeutic effect of the treatment, which is determined by the surgeon performing the treatment.

Throughout the present description, the term "attenuation" has been used. The term absorption could also be used; strictly speaking, absorption only takes into account spreading of heat and other losses in the medium. On the contrary, attenuation is generally calculated from overall weakening of a signal. In practice, the ratio between attenuation and absorption is generally constant for a given tissue.

This invention is obviously not limited to the examples and embodiments described and illustrated, but may be subject to numerous variations accessible to those skilled in the art. It is clear that although the invention was described with reference to the example of the prostate, it is not limited to such an organ, and can apply to other tissue. The invention could thus be used for hyperthermia treatment of the breast, liver, or other organs or tissue. It is also clear that the invention is not limited to the embodiment shown in FIG. 1, and can be applied to endocavital apparatus such as the one disclosed in international application PCT/FR 94/00936.

What is claimed is:

1. A method for treating a biological target by emitting high-intensity focused ultrasound toward a focal point, the method comprising the steps of:

providing an ultrasound apparatus having a wideband ultrasound transducer for emitting the ultrasound;

exciting the ultrasound transducer with a narrow band input signal so that the ultrasound transducer emits focused ultrasound energy in a narrow frequency range, said excitation occurring for a predetermined shot duration;

measuring an attenuation factor of the ultrasound energy transmitted from the ultrasound transducer to the biological target;

calculating an optimum frequency of the input signal supplied to the ultrasound transducer based on the measured attenuation so as to maximize an amount of energy absorbed by the biological target; and adjusting the input frequency of the signal supplied to the transducer based on the calculated optimum frequency.

2. The method according to claim 1, wherein the attenuation of the ultrasound energy returned by the biological target is measured using a reflection method.

3. The method according to claim 1 wherein the attenuation of the ultrasound energy returned by the biological target is measured using a frequency method.

4. The method according to claim 1 wherein the attenuation of the ultrasound energy returned by the biological target is measured by determining variations in an amplitude of frequency components of the ultrasound energy.

5. The method according to claim 1 wherein the attenuation of the ultrasound energy returned by the biological target is measured by determining a shift in a central frequency of the ultrasound energy.

6. The method according to claim 1 wherein the optimum frequency of the signals supplied to the ultrasound transducer is calculated according to the formula:

$$Q = 2\alpha F I_0 \, G e^{-2\alpha F d}$$

where Q is an acoustic power absorbed per unit of volume $\alpha$ is the acoustic attenuation factor (Neper/cm/MHz)

$I_0$ is an acoustic intensity at a transducer emission surface (W/cm$^2$)

G is an antenna gain

F is the input frequency (MHz)

d is the thickness of the absorbing medium (cm)

wherein the measured attenuation factor, $\alpha$, is substituted into said formula and the optimum input frequency, F, is calculated to yield a maximum value of the acoustic power absorbed, Q.

7. The method according to claim 1 wherein the optimum frequency of the signals supplied to the ultrasound transducer is calculated before the shot duration.

8. The method according to claim 1 wherein the optimum frequency of the signals supplied to the ultrasound transducer is calculated during the shot duration.

9. A method for treating a biological target by emitting high-intensity focused ultrasound toward a focal point, the method comprising the steps of:

providing an ultrasound apparatus having an ultrasound transducer for emitting the ultrasound;

exciting the ultrasound transducer with an input signal so that the ultrasound transducer emits focused ultrasound energy in a narrow frequency range, said excitation occurring for a predetermined shot duration;

measuring an attenuation factor of the ultrasound energy transmitted from the ultrasound transducer to the biological target;

calculating an optimum frequency of an input signal supplied to the ultrasound transducer based on the measured attenuation so as to maximize an amount of energy absorbed by the biological target; and adjusting the input frequency of signals supplied to the transducer based on the calculated optimum frequency.

10. A method for treating a biological target by emitting high-intensity focused ultrasound toward a focal point, the method comprising the steps of:

providing an ultrasound apparatus having a wideband ultrasound transducer for emitting the ultrasound;

exciting the ultrasound transducer with a narrow band input signal so that the ultrasound transducer emits focused ultrasound energy in a narrow frequency range, said excitation occurring for a predetermined shot duration;

measuring attenuation of the ultrasound energy transmitted from the ultrasound transducer to the biological target;

calculating an optimum frequency of an input signal supplied to the ultrasound transducer based on the measured attenuation so as to maximize an amount of energy absorbed by the biological target; and modifying the input frequency of signals supplied to the transducer based on the calculated optimum frequency.

11. An apparatus for treating a biological target within a human body, the apparatus comprising:

an wideband ultrasound transducer configured to emit high-intensity focused ultrasound toward a focal point;

a coupler disposed between the ultrasound transducer and the human body to facilitate efficient transmission of the ultrasound to the biological target;

the ultrasound transducer supplied with a narrow band input frequency signal to cause the ultrasound transducer to emit focused ultrasound energy in a narrow frequency range, said emission of ultrasound occurring for a predetermined shot duration;

means for measuring an attenuation of the ultrasound energy transmitted from the ultrasound transducer to the biological target; and wherein an optimum frequency of an input signal supplied to the ultrasound transducer is calculated based on the measured attenuation so as to maximize an amount of energy absorbed by the biological target, and wherein the input frequency of signal supplied to the transducer is adjusted based on the calculated optimum frequency.

12. A method for treating a biological target by emitting high-intensity focused ultrasound toward a focal point, said high-intensity focused ultrasound creating a lesion, the method comprising the steps of:

providing an ultrasound apparatus having a fixed focus ultrasound transducer for emitting the ultrasound;

exciting the ultrasound transducer with a narrow band input signal, said excitation occurring for a predetermined shot duration; and increasing an input frequency the signal supplied to the transducer during the shot duration to effectively treat the biological target—between.

13. The method according to claim 12 wherein the frequency is varied continuously during the shot duration.

14. The method according to claim 12 wherein the frequency is varied continuously during a portion of the shot duration.

15. The method according to claim 12 wherein the frequency is varied according to a plurality of increasing frequency steps during the shot duration.

16. The method according to claim 12 wherein the frequency is varied according to a plurality of increasing frequency steps during a portion of the shot duration.

17. The method according to claim 12 wherein the frequency is varied according to a plurality of increasing non-linear frequency steps during the shot duration.

* * * * *